United States Patent
Regnier et al.

(10) Patent No.: US 12,064,621 B2
(45) Date of Patent: Aug. 20, 2024

(54) IMPLANTABLE MEDICAL DEVICE WITH A FLEXIBLE HELICAL ANCHORING SCREW

(71) Applicant: CAIRDAC S.A.S., Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 29 days.

(21) Appl. No.: 17/982,740

(22) Filed: Nov. 8, 2022

(65) Prior Publication Data
US 2023/0201579 A1 Jun. 29, 2023

(30) Foreign Application Priority Data
Dec. 29, 2021 (EP) ...................... 21315298

(51) Int. Cl.
*A61N 1/05* (2006.01)
*A61N 1/375* (2006.01)
(52) U.S. Cl.
CPC ........... *A61N 1/059* (2013.01); *A61N 1/3756* (2013.01)
(58) Field of Classification Search
CPC ...................................................... A61N 1/059
See application file for complete search history.

(56) References Cited

U.S. PATENT DOCUMENTS

| | | | | |
|---|---|---|---|---|
| 10,391,306 B2 * | 8/2019 | Ma | ........................ | A61N 1/0573 |
| 11,197,997 B2 * | 12/2021 | Regnier | ............. | A61N 1/37518 |
| 2004/0133243 A1 * | 7/2004 | Santamore | ............. | A61N 1/056 607/5 |
| 2009/0259212 A1 * | 10/2009 | Sabbah | .................... | A61M 5/46 604/117 |
| 2011/0307043 A1 * | 12/2011 | Ollivier | .............. | A61N 1/37518 607/127 |
| 2015/0351910 A1 * | 12/2015 | Gilmore | ............. | A61B 17/0401 606/151 |
| 2017/0072191 A1 * | 3/2017 | Ma | ........................ | A61N 1/3756 |
| 2017/0209688 A1 * | 7/2017 | Drake | .................... | A61N 1/057 |
| 2019/0001119 A1 * | 1/2019 | Schmidt | ................... | A61B 6/12 |
| 2020/0094048 A1 * | 3/2020 | Regnier | .............. | A61N 1/0573 |
| 2020/0147365 A1 * | 5/2020 | Marshall | ................ | A61N 1/362 |
| 2020/0306522 A1 * | 10/2020 | Chen | ...................... | A61N 1/059 |
| 2023/0201578 A1 * | 6/2023 | Regnier | ................ | A61N 1/059 607/127 |

FOREIGN PATENT DOCUMENTS

EP 2473228 B1 7/2012

* cited by examiner

*Primary Examiner* — Eric D. Bertram
(74) *Attorney, Agent, or Firm* — CRGO Global; Steven M. Greenberg (57) ABSTRACT

The device has a device body with a front face at its distal end, and a means for the anchoring of the medical device to a patient's organ wall. The anchoring means includes a screw with a helix wire wound into a plurality of non-contiguous turns, the screw having a clamped end integral with the front face of the device body and a free end with a beveled end defined by at least one oblique surface. The helix wire includes, at its free distal end, a terminal region whose wire bending stiffness is lower than in a proximal region of the helix turns. The stiffness difference may, in particular, be obtained by varying the wire diameter over different successive portions, with decreasing diameters in a proximal to distal direction.

11 Claims, 6 Drawing Sheets

IMPLANTABLE MEDICAL DEVICE WITH A FLEXIBLE HELICAL ANCHORING SCREW

CROSS REFERENCE TO RELATED APPLICATIONS

This application claims priority under 35 U.S.C. § 119(a) to European patent application 22153565.1 filed on Jan. 27, 2022, and also to European patent application 21315298.6 filed on Dec. 29, 2022, the entire teachings of which are incorporated herein by reference.

BACKGROUND OF THE INVENTION

Field of the Invention

The present invention relates to implanted medical devices, in particular those which are intended to be implanted into a heart cavity, and more particularly to autonomous implantable devices of the "leadless capsule" type, which are implantable devices having no physical connection (lead) with a remote device, and which are anchored to an implantation site with a helical screw.

Description of the Related Art

In the art of cardiac implantable devices, an implanted capsule continuously monitors the patient's rhythm and, if necessary, issues to the heart electrical pulses for pacing, resynchronization and/or defibrillation in case of rhythm disorders detected by the capsule. The capsule includes various electronic circuits, sensors, etc., as well as wireless communication transmission/reception means for the remote exchange of data, the whole being integrated in a very small size body able to be implanted at sites of difficult access or leaving little available space, such as the ventricle apex, the inner wall of the atrium. In particular, implementing an atrial capsule offers the significant advantage of allowing a pacing of the "dual chamber" type, combining a ventricular capsule with an atrial capsule, both provided with mutual communication means. The atrial capsule detects the atrial depolarizations of the sinus rhythm, and the ventricular capsule, as well as possibly the atrial capsule, issue(s) as needed to the ventricle and/or to the atrium pacing pulses sequenced in such a way as to accurately control the atrioventricular pacing delay.

Generally, an implantable capsule is provided at its distal end with an anchoring member adapted to enter the tissues of a body wall. In the case of an endocavitary capsule, the capsule is fixed to the inner wall of a ventricular or atrial chamber. Several types of anchoring devices exist, often with elastically deformable tines extending into the mass of the myocardium, but also anchoring means implementing a protruding helical screw axially extending the capsule body and adapted to enter the heart tissue at the implantation site by being screwed thereinto.

The "delivery" of the capsule, that is to say, its positioning to the implantation site, consists in mounting the capsule at the end of a guide-catheter of an implantation accessory, then to make it move along the peripheral venous network and to drive it up to the chosen site, for example the apex of the right ventricular chamber. Once the implantation site reached, by means of the guide-catheter, the practitioner imparts to the capsule a combined movement of axial translation (to make the capsule move forward then to exert a pressure against the heart wall) and rotation of the capsule about itself (to screw the anchoring member into the heart wall thickness). Once the capsule firmly anchored, the practitioner proceeds to the "release" of the capsule, i.e. its separation from the implantation accessory, so that the capsule then becomes fully autonomous.

Published international application WO 2002/064172 A1 by Cairdac, corresponding to U.S. Pat. No. 11,197,997 B2 describes a capsule provided with a helical anchoring screw, and further provided with a torque limitation system making it possible to disengage the capsule body from the anchoring screw when the reaction torque exerted by the anchoring screw exceeds a predetermined threshold, in such a way as not to exceed a limit value known as "coring torque" beyond which the anchoring screw would risk to locally tear the tissues under the effect of rotation of the screw without forward move of the latter, until causing a laceration of the tissues and, in the extreme, a piercing of the wall with a risk of tamponade.

European Patent Application Publication EP 2473228 A1 by Friedman et al. discloses another type of anchoring screw for a head of a sensing/pacing lead, adapted to allow a bipolar pacing at the atrioventricular septum. A first electrode is formed by a distal, non-isolated, region of the screw; a coil is wound on the proximal, isolated, region of the screw, and is covered with an isolating sheath, except locally on a median region of the screw which forms a second electrode.

As will be explained in detail hereinafter, this risk of damaging the tissues is particularly high in case of implantation in a thin wall such as that of the atrium, in particular in the region of the right atrial appendage (RAA), considering the very low thickness, typically of the order of 0.5 to 2 mm, according to the location. The difficulty is increased by the fact that the RAA region contains many folds and it is not possible to predict the exact thickness at the implantation site before the screwing and, moreover, in case of piercing of the heart wall, it is not possible to detect a bleeding, the blood effusion occurring inside the pericardial sac (hemorrhagic tamponade). Moreover, due to these folds, it is not possible to determine exactly the angle that the capsule will form with the myocardium at the time of contact with the heart wall. If the direction is oblique, the risk of piercing is lower, but the risk of a wrong detection threshold is higher, and vice versa.

In any case, given the reduced wall thickness, the fixing length of the helix (length of the screw beyond the front flat side of the capsule that supports the sensing/pacing electrode) will necessarily be lower than 1.5 mm, which is a reduced length making it difficult to obtain a reliable and lasting anchoring of the device to the atrium wall.

BRIEF SUMMARY OF THE INVENTION

The invention more particularly relates to the anchoring of the capsule, or more generally the medical device, including capsules intended to diffuse in situ an active pharmacological agent, to the chosen implantation site. The present invention has for object to propose an implantable medical device provided with a screw anchoring allowing a mechanically secure and clinically safe fixing to a thin wall, by making sure not to pass through the thin wall of the organ with helix—in particular, in case of implantation in the atrium, to protect the pericardial space and to prevent any bleeding.

To solve these problems and reach the objects exposed hereinabove, the invention proposes for that purpose an implantable medical device including a device body with a front face at its distal end, and a means for anchoring the medical device to a patient's organ. The anchoring means includes a screw with a helix wire wound into a plurality of non-contiguous turns, the screw having a clamped end integral with the front face of the device body, and a free end with a beveled end defined by at least one oblique surface.

Characteristically of the invention, the helix wire of the screw is a wire that is deformable in bending, and the screw includes, at its free distal end, a terminal region whose helix wire bending stiffness is lower than in a proximal region of the screw turns. That way, during a screwing into an atrial wall, once the visceral pericardium reached, the terminal region at the free distal end of the screw is deformed according to a non-helical geometry, without piercing of the visceral pericardium.

According to various advantageous subsidiary features:
the screw is further elastically deformable in axial compression, in such a way that the screw, once the visceral pericardium reached, produces a crushing of the myocardium without piercing of the visceral pericardium;
the terminal region extends over at least one half-turn of the helix;
the terminal region is a region of non-constant stiffness including a plurality of different successive portions whose respective stiffnesses decrease in a proximal to distal direction;
the terminal region is a region of non-constant stiffness including a helix wire of variable diameter, continuously decreasing in a proximal to distal direction;
in this latter case, the diameter of the helix wire can be in particular a diameter that is variable over a length of one turn of the helix wire, then constant over the next proximal turns of the helix, in particular a diameter that increases by 0.2 mm on the distal side of the terminal end, up to 0.5 mm on the proximal side of the terminal end;
the terminal region is a region of non-constant stiffness, including a plurality of different successive portions of same diameter having undergone heat treatments for modifying their respective stiffnesses;
the helix wire of the screw has a constant no-load winding pitch, or, at least over the length of the terminal region, a variable no-load winding pitch, decreasing in a distal to proximal direction;
the device further includes a disengageable coupling arranged in such a way as, when an external axial rotational stress is applied to the device body in a screwing direction of the screw, to allow a relative axial rotation between the device body and the anchoring means as soon as a reaction torque exerted by the screw in the patient's organ wall exceeds a predetermined threshold torque.

The device according to the invention may in particular be an autonomous cardiac implant of the leadless capsule type, wherein the device body receives an electronic unit and an energy harvesting module with an energy storage means for powering the electronic unit, and wherein the front face of the device body carries a cardiac sensing/pacing electrode adapted to come into contact with the patient's organ wall after anchoring of the device.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 5 is a cross-sectional view of a heart wall, in particular at the atrium, showing in detail the different tissues the wall is formed of.

DETAILED DESCRIPTION OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of implantable devices.

Figure 1:
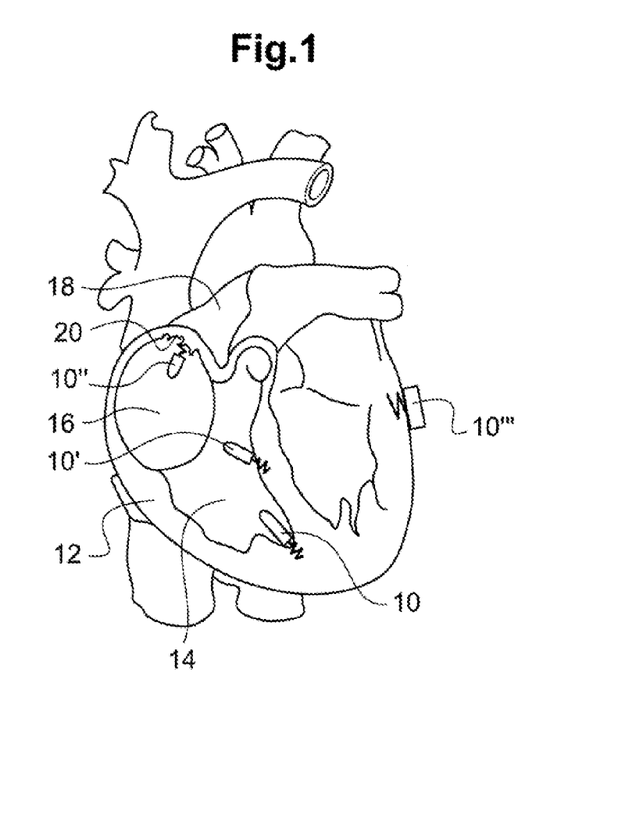
FIG. 1 illustrates medical devices of the leadless capsule type in their environment, with various examples of implantation sites in, on or near a patient's heart.

FIG. 1 shows various possibilities of implantation sites for an implantable medical device of the leadless capsule type, in an application to cardiac pacing. Thus, the capsule denoted 10 is implanted at the apex of the right ventricle 14 of the myocardium 12. The capsule may also be implanted on the interventricular septum, as in 10', or also on a right atrial wall 16, as in 10". The device may also be an epicardial capsule placed on an external region of the myocardium, as illustrated in 10'''.

Hereinafter will be described in more detail, with reference in particular to FIG. 5, the specific case of implantation in the region of the right atrial appendage 18, where the heart wall inside the atrium 16 has a more reduced thickness, as well as a number of folds and trabeculations 20; this region has for advantage not to be in the continuation of the superior vena cava and the tricuspid valve, so that the presence of a capsule at this place won't impede access to the other areas of the atrial or ventricular chambers, in particular to accede to the bottom of the ventricle if it is desired to implant a capsule into the apex region or to explant it therefrom.

In any case, the leadless capsule is fixed to the heart wall by means of a protruding anchoring system entering the heart tissue in order to hold it in place at the implantation site. Various systems can be used, the invention relating more particularly to the capsules provided with a helical screw anchoring member.

Figure 2:
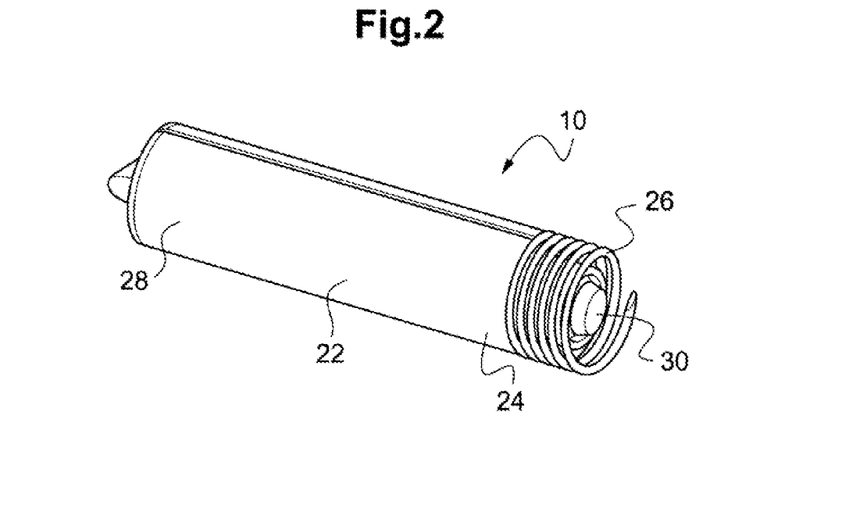
FIG. 2 is an overall external view of a leadless capsule, showing in particular the anchoring screw and the pacing electrode at its distal end.

As illustrated in FIG. 2, a capsule provided with such a member has generally the shape of a tubular body 22 enclosing the various electronic and power supply circuits of the capsule. The typical size of the known capsules is a diameter of the order of 6 mm for a length of about 25 to 40 mm. The tubular body 22 has, at its front (distal) end 24, a cylindrical helical screw 26 intended to hold the capsule in place at the implantation site. The opposite (proximal) rear end 28 is a free end, which is only provided with means (not shown) for the temporary connection to a guide-catheter or another implantation accessory usable for implantation or explanation of the capsule, which is then detached from the latter.

To ensure the sensing/pacing functions, an electrode 30 is arranged on the front face of the capsule; once the capsule anchored at the implantation site, the electrode 30 is in contact with the heart tissue, hence making it possible to collect the cardiac depolarization potential and/or to apply pacing pulses.

Figure 3:
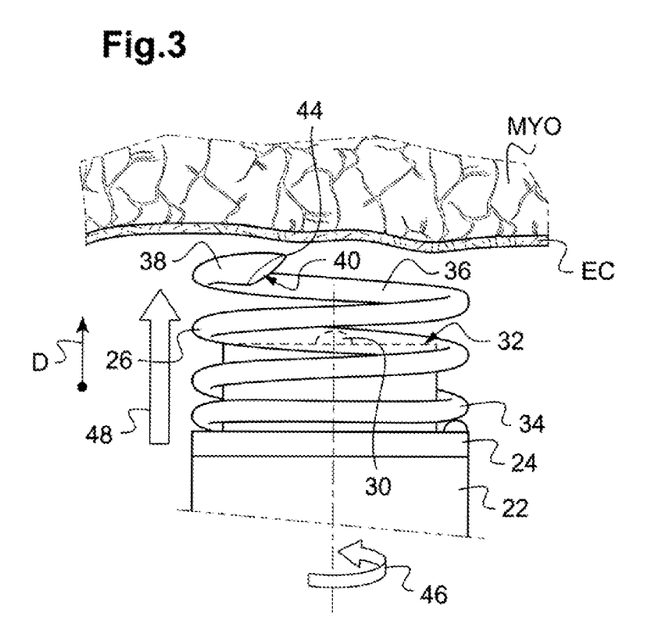
FIG. 3 shows more precisely the distal end of a leadless capsule provided with an anchoring screw according to the state of the art, with the screw end approaching the wall of the implantation site.

FIG. 3 shows more precisely the distal end of the capsule with the helical screw 26 approaching the heart wall, including the myocardium MYO and the endocardium EC.

At the time of implantation, the front face 32 of the capsule body 22, which carries the electrode 30, is turned towards the endocardium wall. The helical screw 26 includes, on the proximal side, inactive turns 34 integral with the body 22 of the capsule, and, on the other side, active turns 36 ended by a beveled free end 38.

Such a capsule is for example described by abovementioned

WO 2002/064172 A1 (U.S. Pat. No. 11,197,997 B2).

Figure 4:
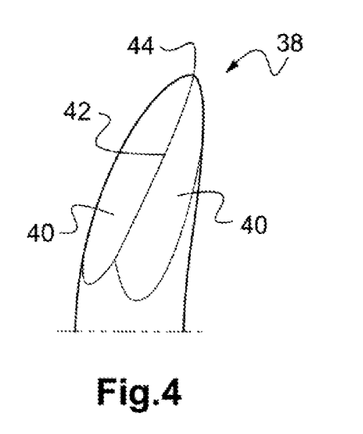
FIG. 4 is a detail view of the beveled end of the anchoring screw of FIG. 3.

FIG. 4 illustrates more precisely the beveled tip 38, which is a piercing tip having one or several oblique surfaces 40 making it possible to create a cutting edge 42 with a piercing tip 44 at the most distal end of the helical screw. As can be seen in FIG. 3, the piercing end 44 is directed towards the heart wall, with the oblique surfaces 40 turned in the proximal direction (the distal direction being denoted by the reference D in FIG. 3).

This configuration with the tip turned towards the wall (that is to say in the distal direction D) facilitates the piercing of the endocardium EC then the penetration into the myocardium MYO in the different configurations liable to be met, even in case of inclination between the capsule axis and the normal to the wall when it comes into contact with the latter. Once the tip 44 in contact with the endocardium EC, the combined movement of rotation 46 and translation 48 (axial thrust) exerted by the practitioner via the guide-catheter ensures the piercing of the endocardium EC and the penetration of the screw into the myocardium MYO over the length of the active turns 36, which is of the order of 1.5 mm or more for a fixing to the ventricular chamber. The front face 32 carrying the electrode 30 is then in contact with the heart wall, allowing the electrode to ensure its sensing/pacing functions.

The known anchorage screw configuration described above with reference to FIGS. 3 and 4 is however ill-suited for a fixing to the atrium, as care must be taken not to pierce the wall.

Figure 5:
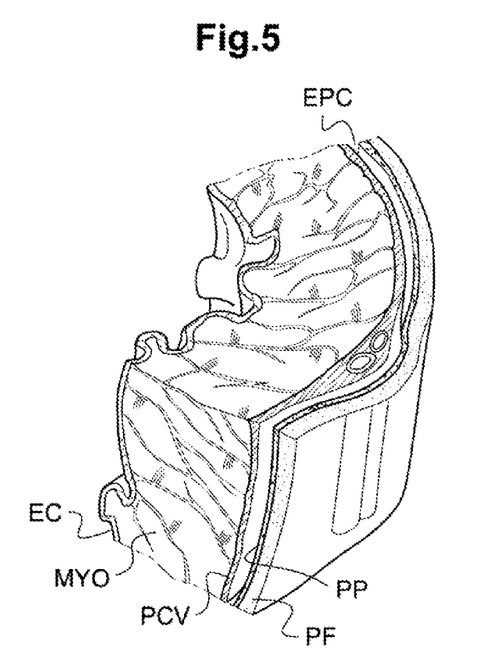

FIG. 5 illustrates the various tissues constituting the heart wall of the atrium, in particular at the right atrial appendage (RAA): the wall includes, from the inside to the outside, the endocardium EC, the myocardium MYO, the visceral pericardium PCV, the pericardial space EPC, the parietal pericardium PP and the fibrous pericardium PF.

The total thickness of the wall is included between 0.5 and 2 mm, hence a far lower value than that of the ventricle, whether it is at the apex or the septum. Moreover, the visceral pericardium PCV is a very thin wall, of about 0.2 mm thick, which is passed through in places by coronary blood vessels. If it is desired to implant into such a wall a capsule provided with a screw-based anchoring member, the visceral pericardium PCV must absolutely not be passed through with the screw helix, in order to avoid any piercing that would create a risk of hemorrhagic tamponade with blood effusion in the pericardial space EPC. However, it is necessary to penetrate sufficiently into the myocardium MYO to guarantee a good fixing of the capsule to the heart wall.

To solve this problem, the invention proposes a new configuration of anchoring screw, illustrated in FIGS. 6 to 16.

Figure 6:
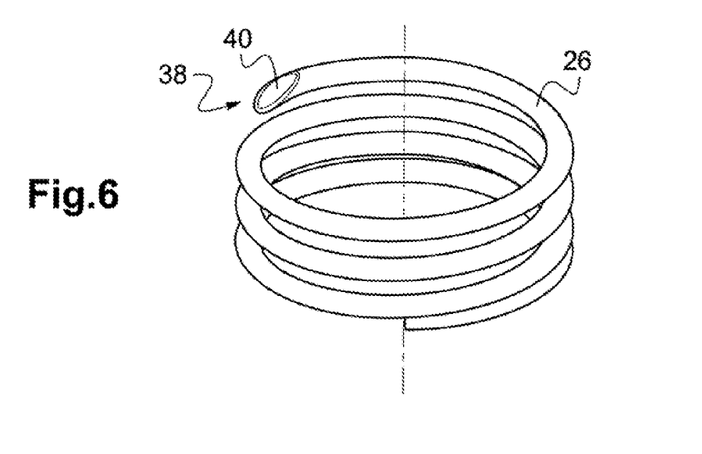
FIG. 6 is a perspective view of an anchoring screw according to the present invention.

As illustrated in FIG. 6, the helical screw 26 is ended by a free beveled end 38 defined by at least one oblique surface 40.

The oblique surface 40 may be a flat surface. It may also be a curved surface, for example a conical surface such as the surface of a cone of revolution or an oblique cone whose region close to the apex would have been blunted not to be traumatic.

Figure 15:
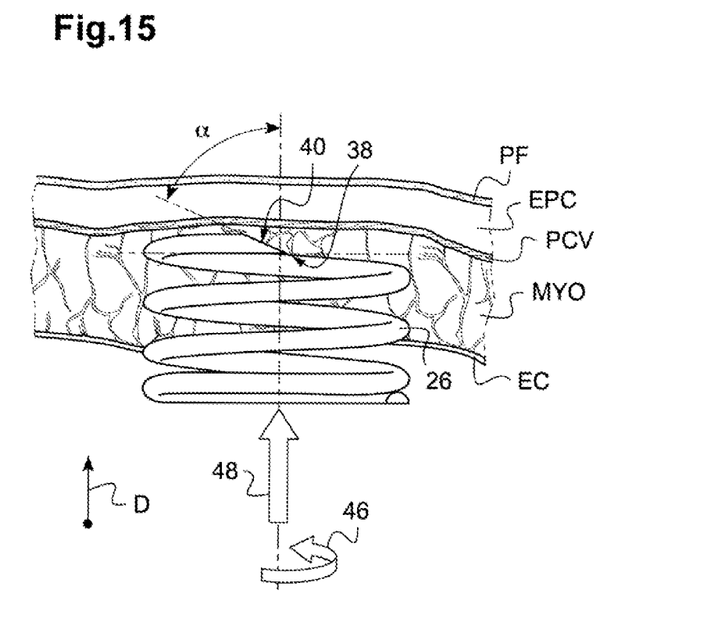
FIG. 15 shows the distal end of an anchoring screw according to the invention, during the penetration of the heart wall at the implantation site.

Very preferentially, the oblique surface 40 defining the bevel of the end 38 is turned towards the wall, that is to say in the distal direction D (cf. FIG. 15). In other words, the normal to the oblique surface 40 is directed away from the front face of the device body, in such a way that this oblique surface 40 is turned towards the organ wall—unlike the anchoring screws of the state of the art, in which the oblique surface of the bevel is directed away from the wall (as illustrated in FIG. 3).

The normal to the oblique surface forms an angle α (cf. FIG. 15) typically between 30° and 60° with respect to the helix axis.

Another preferential feature of the anchoring helical screw according to the invention is that it is elastically deformable in axial compression, with a stiffness coefficient of at most 5 N/mm.

The helix wire may in particular have the following characteristics (which are in themselves non-limiting to the invention):

right winding;

biocompatible material such as stainless steel, titanium, nitinol, etc., advantageously with a coating providing a surface state forming micro-reliefs (titanium nitride coating) or a porosity (by chemical etching) that promote adhesion of the screw to fibrotic tissues after implantation;

wire diameter: 0.2 to 1 mm;

external diameter of the helix: lower than 26 Fr (8.67 mm);

number of active turns: 1 to 5 turns;

no-load winding pitch: 1 mm (the pitch can potentially be a variable pitch);

length of the active turns in the axial direction: lower than 1.5 mm.

Figure 7:
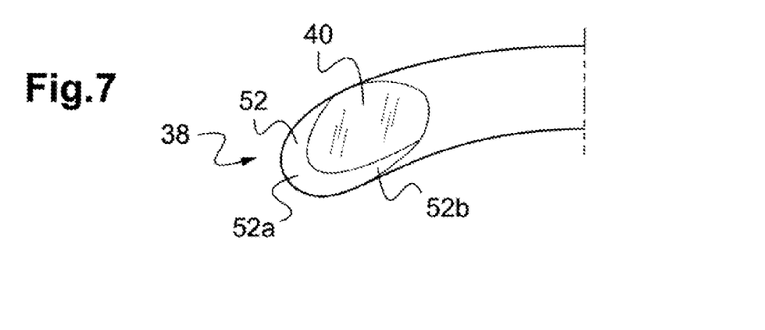
FIG. 7 is a detail view of the distal end of the anchoring screw of FIG. 6.

The beveled end 38 is made by a machining making it possible to shape the oblique surface 40. Advantageously, as illustrated in FIG. 7, a round 52 is made over the periphery of the oblique surface 40, by traditional machining or by laser shooting. The rounded edge 52 allows eliminating the cutting edge (which existed with the helical screws of the prior art as illustrated in FIGS. 3 and 4) and making the geometry of the helical screw end atraumatic. The piercing of the visceral pericardium is hence prevented by eliminating any tip or cutting edge at the end of the helix. Advantageously, the round formed at the end of the helix is a variable round, with a radius value decreasing progressively from the distal end 52a to the less distal region 52b. The round diameter at the distal end 52a is for example of 0.1 mm, generally a round diameter lower than ⅓ of the wire diameter.

Figure 8:
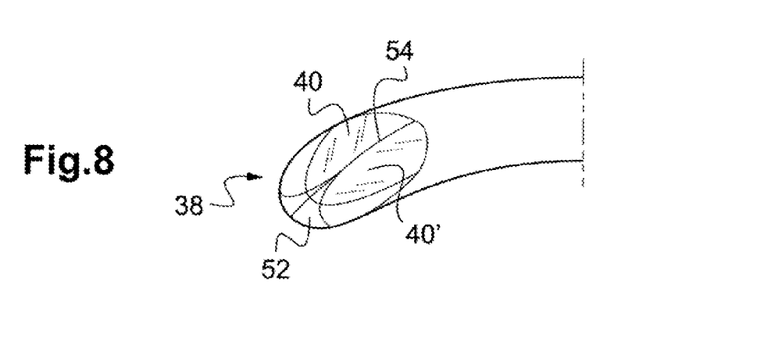
FIG. 8 illustrates an alternative of FIG. 7.

FIG. 8 illustrates an alternative of FIG. 7, in which the beveled end 38 includes two oblique surfaces 40, 40' forming at their intersection an edge 54, also rounded in such a way as not to be sharp.

Figure 9:
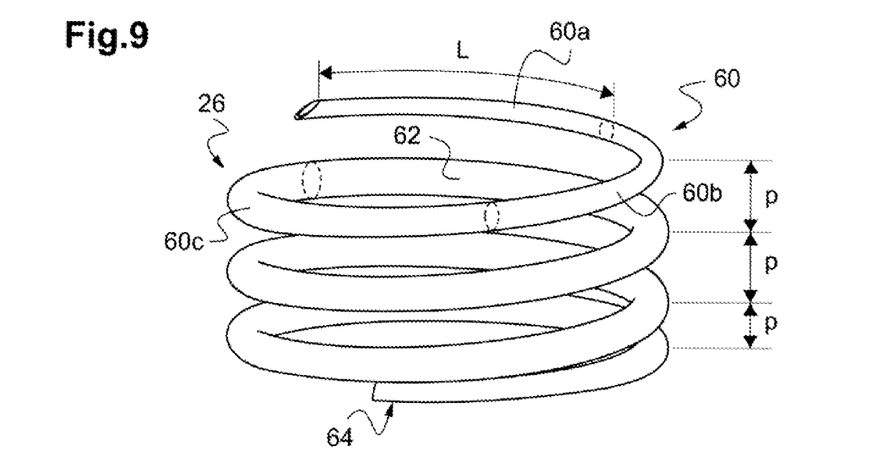
FIG. 9 illustrates an embodiment according to the teachings of the invention, in which the anchoring screw has a bending stiffness that is not constant in a terminal region located near the distal end of the helix.

FIG. 9 illustrates an embodiment according to the teachings of the invention, in which, in a terminal region 60 located in the vicinity of the distal end 38 of the helix, the anchoring screw 26 has a bending stiffness that is not the same as in the most proximal part 62 of the helix.

For that purpose, the wire is consisted of one or several areas having different bending stiffnesses, for example, as in the illustrated example, a juxtaposition of three successive portions 60a, 60b, 60c of different respective stiffnesses, increasing in the distal to proximal direction; that is to say that the wire is more deformable in bending (its stiffness is lower) on the distal side than on the proximal side.

Several embodiments can be contemplated to obtain these different bending stiffnesses in the terminal region.

In the (non-limiting) alternative illustrated in FIG. 9, the terminal part 60 with a lower bending stiffness is consisted of a plurality of wire portions 60a, 60b, 60c, each having a diameter that decreases from its distal end to its proximal end. Still in this alternative, the terminal part 60 includes three wire portions 60a, 60b, 60c of same length L, each extending over one third of a turn. The most distal portion 60a has a wire diameter that increases for example from 0.2 to 0.3 mm in the distal to proximal direction, the intermediate portion 60b a diameter that increases from 0.3 to 0.4 mm, and the most proximal portion 60c a diameter that increases from 0.4 to 0.5 mm. Beyond this portion, in the most proximal part 62 of the helix 26, the wire diameter is a constant diameter of 0.5 mm.

The successive increasing diameters give the wire an increasing corresponding stiffness, for example a stiffness K that varies from 0.1 N/mm (at the most distal end of the helix) to 0.6 N/mm (in the most proximal part, where the diameter of the helix wire is maximum then constant).

The indications and numerical values given above are, of course, for illustrative purposes only and are not in any way limiting.

For example, the variable-stiffness terminal part 60 may extend over more or less than the length of a turn as in the case of FIG. 9.

Likewise, the number of successive portions may be different, for example four sections of a quarter turn each instead of three sections of a third turn, and/or with respective lengths L that are not necessarily identical from one portion to the other.

Figure 10:
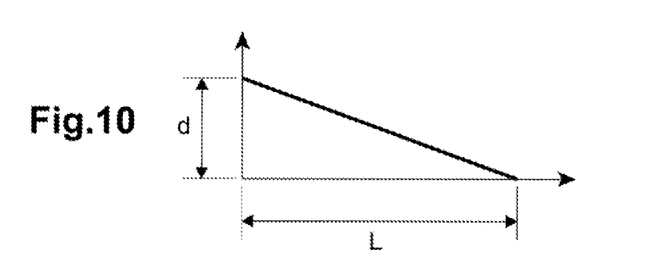
FIGS. 10 and 11 illustrate two possible laws of variation of the bending stiffness over a corresponding fraction of the terminal region.
Figure 11:
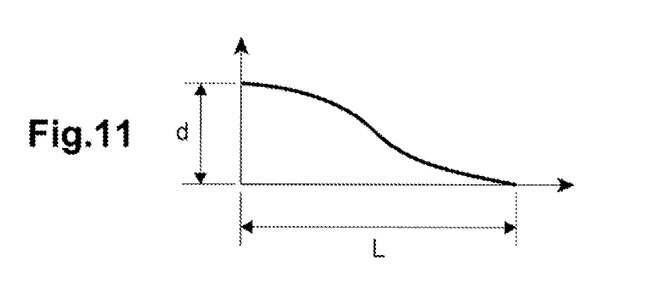

FIGS. 10 and 11 illustrate possible laws of variation of the diameter d over the extent of the length L of one of the wire portions 60a, 60b or 60c. This variation is monotonic and decreasing from the distal to the proximal end of the portion, and follows a law that may be linear (FIG. 10) or not (FIG. 11); in any case, the matter is to ensure a seamless connection with the next section.

It will be noted that, due to the progressive variation of the diameter d, the helix wire of the screw 26 has, over the length of the terminal region 60, a variable no-load winding pitch p, decreasing in the distal to proximal direction.

In another embodiment, the variable stiffness between the terminal part of the helix and the proximal part is obtained with a wire of constant diameter, but with a differentiated treatment according to the regions of the wire, for example a differentiated thermal annealing liable to locally modify the stiffness of the material constituting the wire.

In this case, the no-load winding pitch p is constant but may be made variable, at least over the length of the terminal region 60, decreasing in the distal to proximal direction.

How to make a helix with a locally modified bending stiffness by providing the wire with a variable diameter, as described in FIG. 9, will now be described with reference to FIGS. 12 to 14.

Figure 12:
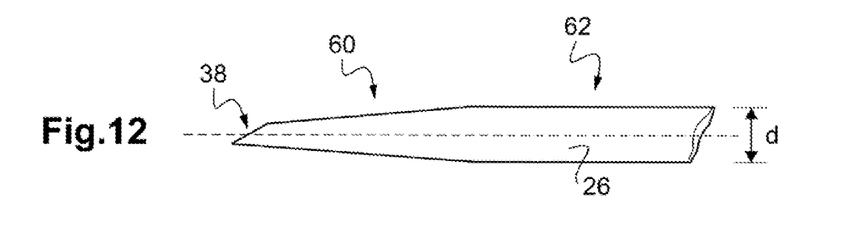
FIG. 12 schematically illustrates the different parts of the helix wire to be machined to obtain a helical anchoring screw with a variable flexion stiffness according to the invention.

The matter is to obtain, as illustrated in FIG. 12 (in which, for the sake of clarity of the figure, the scale in radial direction has been greatly enlarged with respect to the axial direction), a terminal part 60 of variable diameter with, on the distal side, a beveled end 38 and, on the proximal side, the rest of the helix wire 62 with its initial diameter d.

Figure 13:
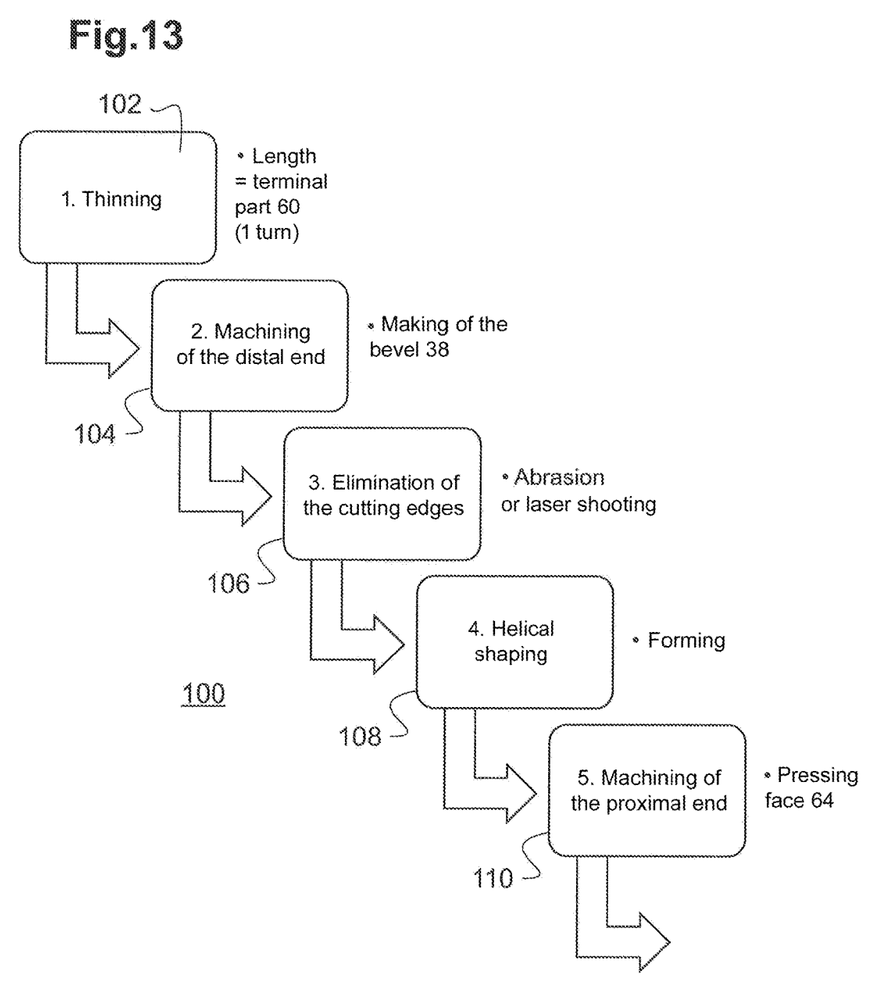
FIG. 13 is a flowchart of a process for obtaining a helical anchoring screw according to the invention.

The succession of steps is illustrated in the process diagram 100 of FIG. 13.

Initially, prior its helical shaping, the wire is a straight wire. The first step 102 consists in performing a progressive thinning of the diameter of this wire over the length of the terminal part of lower stiffness, for example over a wire length that will correspond to a helix turn after helical forming.

This local thinning of the wire in distal part may be performed in various ways.

A first technique consists in performing a traditional machining by a multi-axis translation, rotation and angulation system. The rectilinear wire is placed in a mandrel then rotated, and the thinning is performed by machining after orientation of the tool-holder and positioning of the mandrel-holder. To obtain a profile such as illustrated in FIG. 12, the wire end is thinned into a conical shape, corresponding to the terminal region 60.

Figure 14:
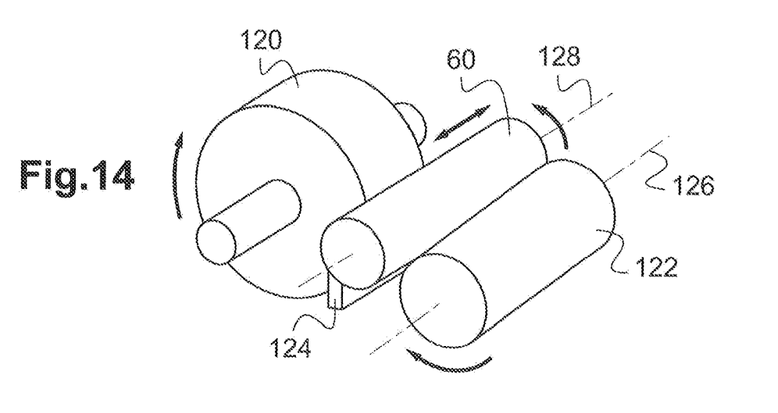
FIG. 14 illustrates an example of tool for carrying out the step of wire thinning of the process of FIG. 13.

Another possibility consists, as illustrated in FIG. 14, in performing a resurfacing between two abrasive rolls 120, 122 turning in opposite directions. The resurfaced wire 60 is positioned on a support 124 for adjustment of the final diameter. To obtain the desired conical shape on the external diameter of the wire 60, the rotation axis 126 of one of the abrasive cylinders 122 is inclined with respect to the axis of rotation 128 of the wire 60.

The following step consists in carrying out the end bevel 38 by material removal (step 104), then eliminating the cutting edges and forming a round by abrasion or by laser shooting (step 106).

The so-prepared wire is shaped into an helix (step 108), by being wound on a traditional spring-making machine.

The process ends by a step 110 of machining the proximal end of the helical screw to form the resting face 64 (FIG. 9) that will come into contact with the distal end 24 of the tubular body 22 of the implantable capsule (FIG. 3).

The way the implantation of the capsule is performed by means of the just-described screw according to the invention will now be explained, with reference to FIGS. 15 and 16.

With this screw, unlike the solutions of the prior art, the end of the helical screw is designed in such a way as not to pierce the heart wall.

The matter is essentially, under the effect of the dual movement of rotation 46 and axial compression 48 imparted by the operator, to make the helix enter the myocardium without cutting the latter (which has very little resistance), then to make the helix end slide on the visceral pericardium PCV without piercing it, thus creating a non-piercing fixing mode. The inclined oblique surface 40 will only push away the visceral pericardium by sliding thereon, without piercing it.

Figure 16:
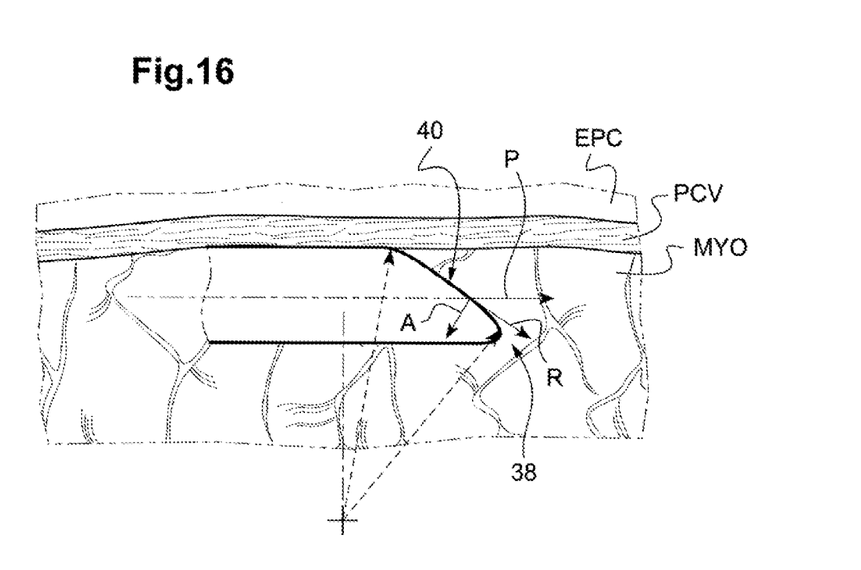
FIG. 16 is an enlarged schematic view of the beveled end of the anchoring screw according to the invention, explaining the different forces exerted at this end, as well as the resultant thereof.

FIG. 16 shows the distribution of the efforts and stresses at the helix end.

In an initial phase, when the helix has entered the myocardium and has not yet reached the visceral pericardium, the axial pressing force on the heart tissue is lower than the axial compression stiffness k of the helix wire. The pressing force A of the oblique surface 40, combined with the radial thrust P produced by the rotation of the screw, produces at the bevel end 38 a resultant R that is insufficient to pass through the visceral pericardium PCV and to risk damaging the latter.

Once the screw has reached the visceral pericardium PCV, the thrust force becomes higher than the stiffness k of the helix wire, due to the fact that the resistance of the visceral pericardium PCV is higher than that of the myocardium MYO. The screw helix will then be compressed, by crushing the myocardium without piercing the visceral pericardium.

Moreover, thanks to the helix wire of variable bending stiffness described hereinabove with reference to FIGS. 9 to 14, once having reached the visceral pericardium, the terminal part of the screw will be deformed according to a non-helical geometry due to the greater flexibility (lower bending stiffness) of its end. The risk of piercing the visceral pericardium is thus significantly reduced, while keeping for the screw good properties of penetration at the time of screwing into the myocardium.

Advantageously, the implant is provided with a torque limiter, made for example according to the teachings of above-mentioned WO 2002/064172 A1 (U.S. Pat. No. 11,197,997 B2), which will allow disengaging the anchoring member from the implant body when the reaction torque exerted by the screw in the organ wall exceeds a predetermined threshold torque, thus avoiding any laceration of the tissues.

The just-described particular helical screw configuration makes it possible to have a "smart", adaptive anchoring helix: in the fragile but more resistant tissue of the pericardium, the risk of piercing is strongly reduced, by keeping a capacity of sliding in the softer tissue of the myocardium. The fixing length of the helix is thus maximized over the almost-totality of the atrium wall thickness, although the latter is thinner and less fragile than in the case of a ventricular implantation.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

The invention claimed is:
1. An implantable medical device intended to be implanted into a thin heart wall of a patient, in particular into an atrial wall comprising successively an endocardium, a myocardium and a visceral pericardium, the device comprising:
 a device body with a front face at its distal end; and
 a means for anchoring the medical device to said heart wall,
 wherein the means for anchoring includes a screw with a helix wire wound into a plurality of non-contiguous turns, the screw having a clamped end integral with the front face of the device body and a free end comprising a beveled end defined by at least one oblique surface,
 wherein the helix wire of the screw is a wire that is deformable in bending,
 wherein the screw comprises, at its free distal end, a terminal region whose helix wire bending stiffness is lower than in a proximal region of the screw turns, in such a way that, during a screwing into an atrial wall, once the visceral pericardium reached, the terminal region at the free distal end of the screw is deformed according to a non-helical geometry, without piercing of the visceral pericardium, and
 wherein the helix wire of the screw has, at least over the length of the terminal region, a variable no-load winding pitch, decreasing in a distal to proximal direction.

2. The device of claim 1, wherein the screw is further elastically deformable in axial compression, in such a way that the screw, once the visceral pericardium reached, produces a crushing of the myocardium without piercing of the visceral pericardium.

3. The device of claim 1, wherein the terminal region extends over at least one half-turn of the helix.

4. The device of claim 1, wherein the terminal region is a region of non-constant stiffness, comprising a plurality of different successive portions whose respective stiffnesses decrease in a proximal to distal direction.

5. The device of claim 1, wherein the terminal region is a region of non-constant stiffness, comprising a helix wire of variable diameter, continuously decreasing in a proximal to distal direction.

6. The device of claim 5, wherein the diameter of the helix wire is variable over a length of one helix wire turn, then constant over the following proximal turns of the helix.

7. The device of claim 5, wherein the diameter of the helix wire increases by 0.2 mm on the distal side of the terminal end, up to 0.5 mm on the proximal side of the terminal end.

8. The device of claim 1, wherein the terminal region is a region of non-constant stiffness, comprising a plurality of different successive portions of same diameter having undergone heat treatments for modifying their respective stiffnesses.

9. The device of claim 1, wherein the helix wire of the screw has a constant no-load winding pitch.

10. The device of claim 1, further comprises a disengageable coupling arranged in such a way as, when an external axial rotational stress is applied to the device body in a screwing direction of the screw, to allow a relative axial rotation between the device body and the means for anchoring as soon as a reaction torque exerted by the screw in the patient's organ wall exceeds a predetermined threshold torque.

11. The device of claim 1, wherein:
the medical device is an autonomous cardiac implant of the leadless capsule type, the device body receives an electronic unit and an energy harvesting module with an energy storage means for powering the electronic unit, and
the front face of the device body carries a cardiac sensing/pacing electrode adapted to come into contact with the patient's organ wall after anchoring of the device.

* * * * *